United States Patent [19]

Crame et al.

[11] Patent Number: 4,496,579

[45] Date of Patent: Jan. 29, 1985

[54] BENZODIOXINOPYRROLE DERIVATIVES AND PROCESSES FOR THEIR PREPARATION

[75] Inventors: Andrew J. Crame, Greenford; Alan D. Borthwick, London, both of England

[73] Assignee: Glaxo Group Limited, London, England

[21] Appl. No.: 545,191

[22] Filed: Oct. 25, 1983

[30] Foreign Application Priority Data

Oct. 25, 1982 [GB]  United Kingdom ............... 8230379

[51] Int. Cl.³ .................... A61K 31/40; C07D 209/48
[52] U.S. Cl. .................................. 514/411; 548/430
[58] Field of Search .................... 548/430; 424/274

[56] References Cited

PUBLICATIONS

Berthold, Helvetica Chimica Acta, vol. 55, 1972, pp. 2461–2467.
Albert Funke, Chem. Abst., vol. 56, 1962, 14257i.
Marini-Bettolo, Chem. Abst., vol. 52, 1958, 16356h.

*Primary Examiner*—Donald G. Daus
*Assistant Examiner*—Cecilia Shen
*Attorney, Agent, or Firm*—Morgan, Finnegan, Pine, Foley & Lee

[57] ABSTRACT

Compounds are disclosed of general formula

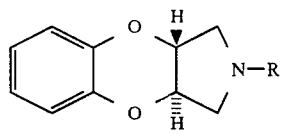

where R is H, $C_{1-6}$ alkyl optionally substituted by $C_{3-7}$ cycloalkyl, $C_{3-6}$ alkenyl or alkynyl, $C_{3-7}$ cycloalkyl, aralkyl or —CHO and the physiologically acceptable salts thereof. The compounds have selective $\alpha_2$-adrenoreceptor antagonist action and are indicated as potentially useful for the treatment or prevention of migraine, thrombosis, diabetes, obesity, hypertension, constipation, paralytic ileus, senile dementia and analepsis, and for use in appetite suppression and for the treatment of depression; they may be formulated as pharmaceutical compositions in conventional manner. The compounds may be prepared, for example, by amination of a compound of formula

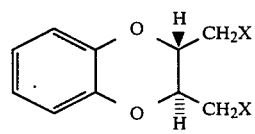

where X is a leaving group such as halogen or a hydrocarbylsulphonyloxy group.

11 Claims, No Drawings

BENZODIOXINOPYRROLE DERIVATIVES AND PROCESSES FOR THEIR PREPARATION

This invention relates to novel benzodioxinopyrrole derivatives, to processes for the preparation thereof, to pharmaceutical preparations containing them, and to their use in medicine.

The alpha ($\alpha$)-adrenoreceptors of the sympathetic nervous system are classified pharmacologically into two sub-groups, namely $\alpha_1$ and $\alpha_2$. The $\alpha_2$-type are situated predominantly on the presynaptic terminals of noradrenergic neurones and are activated by the released neurotransmitter. Such activation results in a diminished release of noradrenaline on subsequent stimulation of the neurones, the $\alpha_2$-adrenoreceptors thus forming part of an autoinhibitory feedback mechanism for regulating the synaptic concentration of the neurotransmitter. A selective $\alpha_2$-adrenoreceptor antagonist would be expected to produce an increase in the synaptic concentrations of noradrenaline by blocking the autoinhibitory feedback mechanism and would thus be of potential value in human medicine for the treatment of disorders such as depression which are associated with a deficiency of noradrenaline at postsynaptic adrenoreceptors.

$\alpha_2$-Adrenoreceptors also occur at non-neuronal sites such as on blood-platelets, in pancreatic islet cells, on adipocytes and in the proximal tubules of the kidney. Activation of $\alpha_2$-adrenoreceptors at these sites leads to platelet aggregation, inhibition of insulin release, inhibition of lipolysis and retention of sodium respectively.

A selective $\alpha_2$-adrenoreceptor antagonist thus has a potential therapeutic use as an antidepressant either alone or in a complimentary combination with an established antidepressant, and in either treating or preventing conditions such as migraine, thrombosis, diabetes, obesity, hypertension, constipation, paralytic ileus, senile dementia and analepsis, and for use in appetite suppression.

We have now found that the compounds of formula (I) below and their physiologically acceptable salts have a selective $\alpha_2$-adrenoreceptor antagonist action.

Certain benzodioxinopyrrole derivatives are described as having been prepared in C.r Seances hebd. Ac. Sci. 1961 253, 1172 by A. Funke and A. Paulsen. Funke et al describe a process starting from a meso-dibromosuccinate which is presumed by Funke et al to yield a cis-benzodioxan dicarboxylate following the process described by Kao et al (Hua Hsueh Hsueh Pao 1957 23 480; Chem. Abs. 1958 52 16356h). Kao et al reported the preparation of cis- and trans-dl-benzodioxan dicarboxylates by reaction of catechol with meso- and dl-dibromosuccinates.

Funke et al then converted their intermediate product into what are described as tetrahydrobenzodioxinopyrroles. The stereochemistry of these compounds was not specified but would have been expected to be cis, as in the starting dicarboxylate.

Subsequently, Berthold et al (Helv. Chim. Acta 1972 55 2461) have demonstrated that the reaction of catechol with the meso-dibromosuccinate affords a benzodioxole rather than a benzodioxan. In addition Berthold et al demonstrated that this product is converted into a tetrahydrospirobenzodioxolopyrrole rather than a tetrahydrobenzodioxinopyrrole as believed by Funke et al.

We have repeated the process described by Funke and, as a result, we are able to confirm and extend the observations of Berthold et al. Thus, we have demonstrated that the reaction of catechol with either the meso- or the dl-dibromosuccinates results in the same compound to which we assign unambiguously the benzodioxole structure. This compound is further converted to provide compounds to which we assign the tetrahydrospirobenzodioxolopyrrole ring system rather than the tetrahydrobenzodioxinopyrrole system.

To summarise, the prior art literature contains reference only to the preparation of compounds which can be construed as cis-compounds. Furthermore, although the compounds are described as tetrahydrobenzodioxinopyrroles this has been shown by Berthold and ourselves to be erroneous due to a previous misassignment of the structure of the starting material.

Furthermore, the prior art references are limited to a purely chemical discussion and there is no mention that any of the compounds prepared or said to be prepared have any biological activity.

The invention thus provides compounds of general formula (I)

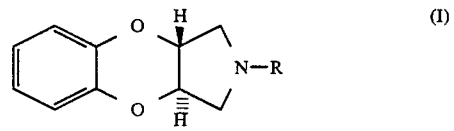

wherein R is a hydrogen atom or a $C_{1-6}$ alkyl (optionally substituted by $C_{3-7}$ cycloalkyl), $C_{3-6}$ alkenyl, $C_{3-6}$ alkynyl, $C_{3-7}$ cycloalkyl, aralkyl (in which the alkyl moiety contains 1-5 carbon atoms), or —CHO group, and the physiologically acceptable salts thereof.

In the above definitions of general formula (I), the alkyl, alkenyl and alkynyl groups may be straight or branched chains. When R contains a —C=C— or —C≡C— linkage this is not directly attached to the nitrogen atom. When R is alkyl it may be, for example, methyl, ethyl or propyl, methyl being preferred. When R is an alkyl group substituted by a $C_{3-7}$ cycloalkyl group it may be, for example, cyclopropyl $C_{1-3}$ alkyl such as cyclopropylmethyl. When R is alkenyl it may be, for example, allyl and when R is alkynyl it may be, for example, propynyl. When R is cycloalkyl it may be, for example, cyclopropyl. When R is an aralkyl group it may be, for example, phen$C_{1-5}$alkyl, such as benzyl.

Suitable physiologically acceptable salts are the acid addition salts formed with inorganic acids, for example hydrochlorides, hydrobromides, phosphates and sulphates, and with organic acids, for example citrates, tartrates, acetates, maleates and succinates. The hydrochlorides are particularly useful.

It will be appreciated that each compound of general formula (I) is a trans isomer and exists as two enantiomers. The structural formulae herein are to be understood to depict either or both enantiomers of each of the compounds concerned as well as mixtures of the enantiomers, including racemates, even though the precise structure as set out only relates to one enantiomer.

A preferred group of compounds of general formula (I) is that wherein R is a hydrogen atom. Another preferred group of compounds of general formula (I) is that wherein R is a $C_{1-3}$ alkyl group, particularly a methyl or ethyl group.

Particularly important compounds are ($\pm$) trans-2,3,3a,9a-tetrahydro-2-methyl-1H-[1,4]-benzodioxino-[2,3-c]pyrrole; ($\pm$) trans-2,3,3a,9a-tetrahydro-1H-[1,4]- benzodioxino[2,3-c]pyrrole; (3aR-trans)-(+)-2,3,3a,9a-tetrahydro-1H-[1,4]-benzodioxino[2,3-c]pyrrole; (3aS-trans)-(−)-2,3,3a,9a-tetrahydro-1H-[1,4]-benzodioxino[2,3-c]pyrrole; and their physiologically acceptable salts, particularly the hydrochlorides.

A compound of particular interest is (±) trans-2,3,3a,9a-tetrahydro-1H-[1,4]-benzodioxino[2,3-c]pyrrole, hydrochloride.

The compounds of the invention have selective $\alpha_2$-adrenoreceptor antagonist action. The test for determining the $\alpha_2$-adrenoreceptor antagonist action is based on the ability to prevent the action of the selective $\alpha_2$-adrenoreceptor agonist clonidine on the rat field stimulated vas deferens preparation.

Clonidine inhibits the twitch response of the rat isolated vas deferens to low frequency motor nerve stimulation. This inhibition is a consequence of activation of presynaptic adrenoreceptors of the $\alpha_2$-type. Antagonism of the effect of clonidine is quantified by measuring the parallel shift to the right of the inhibitory clonidine $\log_{10}$(concentration)/response curve in the presence of increasing concentrations of the antogonist. Potency and competitiveness of antagonism are determined by the method of Arunlakshana & Schild (Br.J.Pharmac. 1959, 14 48–58).

The $\alpha$-adrenoreceptor-type selectivity of the compounds of general formula (I) is similarly assessed by measuring the ability to produce a parallel shift to the right of the $\log_{10}$ (concentration)/response curve for the $\alpha_1$-adrenoreceptor agonist phenylephrine. The $\alpha_1$-adrenoreceptor-mediated responses of phenylephrine measured were contractions of the rat isolated anococcygeus muscle (Leighton, Butz & Parmeter, Eur. J. Pharmac., 1979, 58 27–38).

The compounds of the invention are thus of interest in the treatment or prevention of migraine, thrombosis, diabetes, obesity, hypertension, constipation, paralytic ileus, senile dementia and analepsis, and for use in appetite supression, and in particular for the treatment of depression.

The invention accordingly further provides compounds of general formula (I) and their physiologically acceptable salts for use in the therapy or prophylaxis of migraine, thrombosis, diambetes, obesity, hypertension, constipation, paralytic ileus, senile dementia, analepsis, appetite supression and, in particular depression. The compounds of the invention may be used either alone or with an additional active ingredient. Thus, for example, in the treatment of depression, the compound of the invention may be used alone, or may be co-administered with an established antidepressant (e.g. desmethylimipramine, imipramine or amitriptyline) either in a single formulation or, preferably, in separate formulations. The established antidepressant can be used in accordance with conventional practice.

The compounds according to the invention may be formulated in a conventional manner, optionally together with one or more other active ingredient, for administration by any convenient route for example for oral, rectal, intravenous or intramuscular administration.

Thus according to another aspect, the invention provides a pharmaceutical composition comprising a compound of general formula (I) and/or a physiologically acceptable salt thereof together with a physiologically acceptable carrier or excipient. The composition may optionally contain an additional active ingredient, for example an antidepressant such as desmethylimipramine, imipramine or amitriptyline.

For oral administration, the pharmaceutical composition may take the form of, for example, tablets, capsules, powders, solutions, syrups or suspensions prepared by conventional means with physiologically acceptable excipients.

Compositions for rectal administration may be in the form of suppositories using a conventional suppository excipient.

The compounds may be formulated for intravenous or intramuscular administraction in dry form for reconstitution before use, or as a sterile solution or suspension.

A proposed daily dose for administration to man is 0.01 to 10 mg/kg, for example 0.05 to 3 mg/kg, which may be conveniently administered in 1 to 3 doses per day. The precise dose administered will of course depend on the age and condition of the patient.

The compounds according to the invention may be prepared by a number of processes. In the following description the group R is as previously defined for general formula (I) except where otherwise indicated.

According to a first example, a compound of general formula (I) may be prepared by amination of a compound of formula (II)

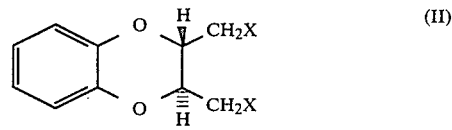

where X is a leaving group such as a halogen atom, (e.g chlorine, bromide or iodine), or a hydrocarbylsulphonyloxy group e.g. methylsulphonyloxy, with ammonia, aqueous ammonia or an amine of formula $RNH_2$, where R is as previously defined except that R is not a hydrogen atom or the group —COH.

In a particular embodiment of this process, following the amination reaction the resulting compound of general formula (I) or a salt thereof may be converted into another compound of general formula (I). Thus, for example, when R is arylmethyl, the amination reaction may optionally be followed by removal of the arylmethyl group to yield a compound of formula (I) where R is a hydrogen atom.

The amination reaction is conveniently effected at an elevated temperature e.g. reflux or sealed tube at e.g. 110° C., preferably in the presence of a suitable base e.g. an excess of the amine $RNH_2$, sodium hydride or an alkali metal hydroxide such as sodium hydroxide, optionally in the presence of a solvent such as an ether e.g. dioxan, chlorinated hydrocarbon e.g. chloroform or an alcohol e.g. ethanol. Optional removal of an arylmethyl group may be carried out for example by hydrogenolysis or, where appropriate, under acidic conditions, as described below.

According to another example, a compound of general formula (I) where R represents a hydrogen atom may be prepared by deprotection of a corresponding compound where R represents a protecting group. Suitable protecting groups include, for example, arylmethyl and acyl groups. Conventional deprotection procedures may be used. For example, where appropriate an arylmethyl group (e.g. benzyl) may be removed by hydrogenolysis using, for example, hydrogen in the presence of a catalyst, such as platinum or palladium on a support (e.g. charcoal), in a solvent such as an alcohol e.g. methanol. Alternatively, where appropriate, an arylmethyl group (e.g. trityl) may be removed under acidic conditions, using for example an acid such as trifluoroacetic acid, formic acid or HBr. Acyl groups may be removed by hydrolysis using an acid such as a mineral acid or a base such as an alkali metal hydroxide as appropriate. The protected starting materials for this process may be prepared using standard methods for the protection of amines, for example as described by J. F. W. McOmie in "Protective Groups in Organic Chemistry" (Plenum Press, 1973).

According to a further example, a compound of general formula (I) where R represents an alkyl group may be prepared by reduction of the corresponding compound in which R is an acyl group using a reducing agent such as lithium aluminium hydride or diborane in a suitable solvent such as ether or tetrahydrofuran at an elevated temperature e.g. reflux. Suitable acyl groups are, for example, formyl, acetyl, or carbonyloxyalkyl e.g. carbonyloxymethyl. The intermediate starting materials for this reaction may be prepared by acylation using conventional methods of a compound of formula (I) in which R represents a hydrogen atom, for example by reaction of the compound of formula (I) with an acid chloride, acid anhydride, or ester.

It is also possible to prepare a compound of general formula (I) by a process comprising interconversion of another compound of general formula (I).

For example, a compound of general formula (I) in which R is a hydrogen atom may be converted by alkylation to a compound of general formula (I) in which R is an alkyl, substituted alkyl, alkenyl, alkynyl or aralkyl group. Conventional alkylation procedures may be used, for example reductive alkylation using an appropriate aldehyde with a complex metal hydride such as sodium or potassium borohydride or sodium cyanoborohydride in a suitable solvent such as an alcohol e.g. methanol. Alternatively, the alkylation may be performed with an alkylating agent $R_2X$ (where $R_2$ is an alkyl, substituted alkyl, alkenyl, alkynyl or aralkyl group and X is a leaving group such as a halogen atom e.g. chlorine or bromine, or a hydrocarbylsulphonoxy group e.g. p-toluene-sulphonyloxy) preferably in the presence of a base, such as potassium carbonate, optionally in a solvent such as an alcohol, e.g. ethanol.

Another example of this embodiment is the preparation of a compound of general formula (I) where R is a group —CHO, which may be prepared by acylation of a corresponding compound of formula (I) in which R is a hydrogen atom using an appropriate acylating agent such as an ester, e.g. an alkyl formate such as methyl formate.

Physiologically acceptable salts of the compounds of general formula (I) may be prepared by reacting the free base of formula (I) or a salt thereof with an appropriate acid, such as hydrogen chloride in the presence of a suitable solvent e.g. ethyl acetate, ether or $CH_2Cl_2$ to obtain the desired physiologically acceptable salt.

The intermediate compounds of general formula (II) may be prepared by reaction of the corresponding diol of formula (III)

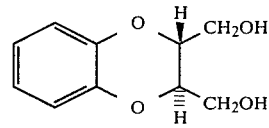

with a halide of formula $X_1A$ (where $X_1$ is a hydrocarbylsulphonyloxy group e.g. methylsulphonyloxy and A is a halogen atom e.g. chlorine) in the presence of a base e.g. triethylamine in a solvent such as dichloromethane; or with a halogenating agent such as thionyl chloride, phosphorous tribromide or hydrogen iodide.

The trans diol of formula (III) is a novel compound and forms a further aspect of the invention.

The diol (III) may be prepared by reduction of the corresponding diethyl ester of formula (IV):

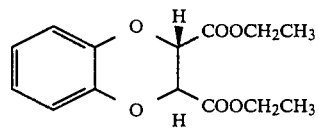

using for example lithium aluminium hydride in tetrahydrofuran at 0° C.

The diethyl ester (IV) may be prepared from the cis-isomer of formula (V)

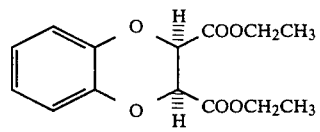

by base catalysed equilibration using for example sodium carbonate in a solvent such as ethanol at room temperature. The mixture of cis and trans isomers so obtained may be separated by conventional means for example by chromatography on silica gel using an eluant such as a mixture of petroleum ether and ethyl acetate.

The cis-isomer of formula (V) may be prepared by catalytic hydrogenation of the diester of formula (VI)

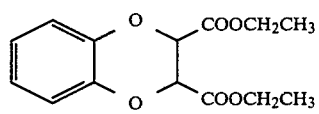

using for example hydrogen in the presence of palladium on charcoal in a solvent such as ethanol at room temperature.

The diester of formula (VI) may be obtained from a diacid of formula (VII):

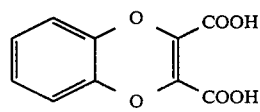

by esterifying the diacid (VII), for example, by refluxing with ethanolic hydrogen chloride. The diacid (VII) may be obtained from benzodioxin-2-carboxylic acid of formula (VIII)

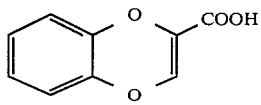

(VIII)

Reaction of the compound (III) (Lalloz et al J. Med. Chem. (1981), 24 994) with lithium diisopropylamide followed by carbon dioxide provides the diacid of formula (II).

To obtain a specific enantiomer of general formula (I), a diol of formula (III) having the required stereochemical configuration should be used in the above processes.

The enantiomeric diol starting material can be prepared from the appropriate dibenzyl threitol of formula (IXa) or (IXb)

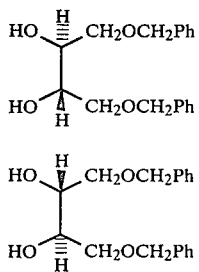

using the following sequence (one enantiomer only shown);

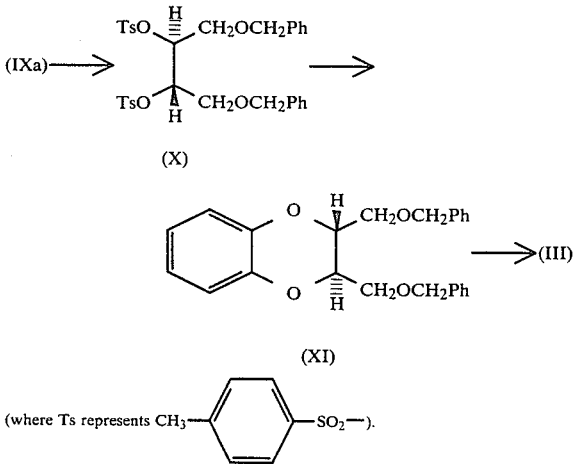

Thus, reaction of the enantiomer (IXa) with 4-toluenesulphonyl chloride in pyridine yields the bis-tosylate (X) which on heating with catechol in acetonitrile containing cesium fluoride gives the benzodioxin (XI) which may be converted to the enantiomeric diol (III) using hydrogen and palladium on charcoal with an ethanol solvent. Use of the enantiomer (IXb) in the same sequence yields the other required enantiomer of formula (III).

The S,S,-enantiomer of formula (IX) is a known compound; and the R,R-enantiomer may be prepared by methods analogous to those for preparing the S,S-enantiomer.

A specific enantiomer of general formula (I) may also be prepared by resolution of a mixture of enantiomers of formula (I) by conventional methods, e.g. by salt formation with an optically active acid followed by separation of the resulting diastereoisomeric salts, e.g. by fractional crystallisation. Alternatively, resolution may be effective at any suitable intermediate stage.

The following Examples illustrate the invention. All temperatures are in °C. "Dried" refers to drying with $MgSO_4$ unless otherwise stated. Chromatography was carried out on silica gel.

The following abbreviations are used:
THF—Tetrahydrofuran
EA—Ethyl acetate
ER—Ether
PE—Petroleum ether (bp 40°–60°)
DMSO—Dimethylsulphoxide
TFA—Trifluoroacetic acid.

INTERMEDIATE 1

[2S-(R*,R*)]-(−)-1,4-Bis(phenylmethoxy)butane-2,3-diol, bis(4-methylbenzenesulphonate)

Toluene-4-sulphonyl chloride (6.0 g) was added to an ice cooled solution of [2S-(R*,R*)]-(−)-1,4-bis(phenylmethoxy)butane-2,3-diol (4.0 g) in pyridine (50 ml) and the mixture was stirred at ambient temperature for 4 days. The mixture was poured into EA and the solution was washed, successively, with 2N-hydrochloric acid, saturated $NaHCO_3$ and water. The solution was dried, evaporated and the residue triturated under ER. The solid was collected, washed with ER and dried in vacuo to yield the title compound 5.6 g as a white solid m.p. 125°–127°. $[\alpha]_D^{23} = -15.5°$ (c 0.97, $CHCl_3$).

INTERMEDIATE 2

(2R-trans)-(+)-2,3-Bis[(phenylmethoxy)methyl]-2,3-dihydro-1,4-benzodioxin

A mixture of catechol (0.54 g) and Intermediate 1 (2 g) in dry acetonitrile (40 ml) was stirred under nitrogen and was warmed until a clear solution was obtained. Cesium fluoride (0.95 g) was added and the mixture was heated at reflux for 3 days, with additional batches of cesium fluoride being added after 3 h (0.95 g), 24 h (1.9 g) and 48 h (1.9 g). After the dark brown mixture had cooled, the solution was decanted and was evaporated to dryness. The combined residues were suspended in EA and the mixture was washed with 2N NaOH solution. The washings were re-extracted with EA and the combined ethyl acetate solutions were filtered and washed with brine. The solution was dried and the solvent was evaporated. The residue was suspended in ER and filtered and the filtrate was chromatographed using a mixture of PE and ER as eluant. Fractions containing the product were combined and evaporated to give the title compound 0.37 g as a clear oil $[\alpha]_D^{23} = +36.2°$ (c 0.91, $CHCl_3$). NMR ($CDCl_3$) τ3.0 to 3.3 (m, 4H, aromatic), 2.69 (S, 10H, Ph—$CH_2$—), 5.38 and 5.54 (ABq, J12, 4H, Ph$\underline{CH}_2$), 6.22 (m, 4H, —$CH_2O$—), 5.69 (m, 2H, ring protons).

INTERMEDIATE 3

(2R-trans)-(+)-2,3-Dihydro-1,4-benzodioxin-2,3-dimethanol

A solution of Intermediate 2 (5.50 g) in ethanol (300 ml), was hydrogenolised at ambient temperature and pressure, using 10% palladium on charcoal (0.5 g) as catalyst, until hydrogen uptake ceased. The catalyst was filtered off, washed well with ethanol and the combined filtrate and washings evaporated. The residue was triturated with ER, the solid was collected, washed with ER and dried in vacuo to afford the title compound 1.81 g, mp 128°–129.5°. $[\alpha]_D^{23} = +54.4°$ (c 1.01, CHCl$_3$).

INTERMEDIATE 4

(2R-trans)-(+)-2,3-Dihydro-1,4-benzodioxin-2,3-dimethanol dimethanesulphonate

A solution of methane sulphonyl chloride (1.90 ml) in CH$_2$Cl$_2$ (50 ml) was added, over 0.25 h, to an ice cooled solution of Intermediate 3 (2.10 g) and triethylamine (4.60 ml) in CH$_2$Cl$_2$ (50 ml). The resulting solution was stirred for a further 0.25 h then washed successively with water, 2N-hydrochloric acid, saturated NaHCO$_3$ and brine. The solution was passed through phase-separating paper and the solvent evaporated. The residue was then triturated under ER, the solid was collected, washed with ER and dried in vacuo to give the title compound 3.5 g as a white solid m.p. 90°–92°. $[\alpha]_D^{23} = +23.1°$ (c 1.3, CHCl$_3$).

INTERMEDIATE 5

(4R-trans)-(+)-4,5-Bis[(phenylmethoxy)methyl]-2,2-dimethyl-1,3-dioxolane

A solution of (4R-trans)-(−)-2,2-dimethyl-1,3-dioxolane-4,5-dimethanol (51 g) in THF (400 ml) was added dropwise to a stirred suspension of sodium hydride (17.5 g of 80% in oil) in THF (200 ml). After 0.75 h, benzyl bromide (116.3 g) was added dropwise and the resulting mixture was stirred for 18 h, and was then heated at reflux for 2 h. After stirring for a further 20 h at 20°, the mixture was cooled in ice, water (10 ml) was added and the mixture was evaporated to dryness. The residue was extracted with ER, and the organic solution was dried and the solvent was evaporated giving a crude product (130 g) which was used without further purification.

INTERMEDIATE 6

[2R-(R*,R*)]-(+)-1,4-Bis(phenylmethoxy)butane-2,3-diol

A solution of Intermediate 5 (130 g) in 0.5N hydrochloric acid (40 ml) and methanol (400 ml) was heated gently, and the acetone/methanol mixture was distilled out over 5 h. The mixture was concentrated, neutralised with NaHCO$_3$ solution and was extracted with EA. The solution was dried and the solvent was evaporated. The product was triturated with ER and PE to give the title compound 69 g, m.pt. 44°–45°, $[\alpha]_D^{21} = +5.4°$ (c, 0.84, CHCl$_3$).

INTERMEDIATE 7

[2R-(R*,R*)]-(+)-1,4-Bis(phenylmethoxy)butane-2,3-diol, bis (4-methylbenzenesulphonate)

To a solution of Intermediate 6 (32.7 g) in pyridine (400 ml), cooled in ice, was added toluene-4-sulphonyl chloride (49 g) and the mixture was stirred at 20° for 4 days. The mixture was cooled in ice, and 10 ml of water was added dropwise, followed by a further 1 liter of water. The precipitate was collected, washed with water and dried to give the title compound, 56.3 g, m.pt. 123°–125°, $[\alpha]_D^{22} = 14.7°$ (c 0.89, CHCl$_3$).

INTERMEDIATE 8

(2S-Trans)-(−)-2,3-Bis[(phenylmethoxy)methyl]-2,3-dihydro-1,4-benzodioxin

A mixture of catechol (8.1 g) and Intermediate 7 (30 g) in dry acetonitrile (600 ml) was stirred under nitrogen and was warmed until a clear solution was obtained. Cesium fluoride (16.6 g) was added and the mixture was heated at reflux for 3 days, with additional batches of cesium fluoride being added after 20 h (7 g), 28 h (7.4 g) and 44 h (7.2 g) and 52 h (7.5 g). After the dark brown mixture had cooled, the solution was decanted and was evaporated to dryness. The combined residues were suspended in EA and the mixture was washed with 2N NaOH solution. The washes were re-extracted with EA and the combined EA solutions were filtered and washed with brine. The solution was dried and the solvent was evaporated. The crude product was purified by chromatography to give the title compound 6 g, $[\alpha]_D^{20} = -38°$ (c 1.2; CHCl$_3$).

INTERMEDIATE 9

(2S-trans)-(−)-2,3-Dihydro-1,4-benzodioxin-2,3-dimethanol

A solution of Intermediate 8 (5.9 g) in ethanol (250 ml) was stirred with 10% palladium on charcoal and was hydrogenated at atmospheric pressure. The calculated amount of hydrogen had been taken up after 5 hours. The mixture was filtered, and the solvent was evaporated giving a crude solid. Purification by trituration with PE gave the title compound as a white solid (2.1 g). $[\alpha]_D^{21} = -54.2°$ (c 0.81, EtOH), $\tau$(CDCl$_3$+DMSOd$_6$) 3.14 (s, 4H, aromatic), 5.50 (t, J6, 2H, OH), 5.88 (m, 2H, CHCH$_2$) and 6.07 (m, 4H, CH—CH$_2$).

INTERMEDIATE 10

(2S-trans)-(−)-2,3-Dihydro-1,4-benzodioxin-2,3-dimethanol dimethanesulphonate

A solution of methanesulphonyl chloride (1.8 ml) in dichloromethane (50 ml) was added, over 0.25 h, to an ice cooled solution of Intermediate 9 (2 g) and triethylamine (4.3 ml) in CH$_2$Cl$_2$ (50 ml). The resulting solution was stirred for a further 0.25 h and then washed successively with water, 2N-hydrochloric acid, saturated NaHCO$_3$ and brine. The solution was passed through phase-separating paper and the solvent was evaporated. The residue was then triturated under ER, the solid was collected, washed with ER and dried in vacuo to give the title compound 3.2 g, m.p. 86°–89°, $[\alpha]_D^{24} = -26.6°$ (c 1.3, CHCl$_3$).

INTERMEDIATE 11

1,4-Benzodioxin-2,3-dicarboxylic acid n-Butyl lithium (185 ml, of a 1.42M solution in hexane) was added to a solution of diisopropylamine (37.0 ml), in dry THF (300 ml) at −78° and the the solution was stirred for 0.25 h. A solution of 1,4-benzodioxin-2-carboxylic acid (23.40 g) in dry THF (400 ml) was then added over 0.5 h and the resulting solution was stirred at −78° for 1 h. The solution was then poured onto finely crushed CO$_2$ and the mixture left to stand overnight. The mixture was evaporated and 2N-hydrochloric acid (250 ml) was added cautiously, followed by concentrated hydrochloric acid (40 ml). EA (500 ml) and THF (100 ml) were added to the mixture, which was shaken and the organic layer separated. The aqueous phase was further extracted with EA and the combined extracts were dried. Evaporation of the solvent gave an orange solid which was triturated under ER for 0.5 h. The solid was collected, washed with ER and dried in vacuo to afford the title compound (25.0 g) m.p. 215°–218°.

INTERMEDIATE 12

1,4-Benzodioxin-2,3-dicarboxylic acid, diethyl ester

Intermediate 11 (24.00 g) was suspended in ethanol (300 ml) and dry HCl was passed through the mixture for about 0.2 h. The resulting solution was heated under reflux for 3 h, cooled and evaporated. The residual oil was dissolved in EA, washed with saturated NaHCO$_3$ solution, dried and evaporated to give the title compound (26.1 g) as a brown crystalline solid m.p. 35°–37°.

INTERMEDIATE 13 cis 2,3-Dihydro-1,4-benzodioxin-2,3-dicarboxylic acid, diethyl ester

A solution of Intermediate 12 (5.00 g) in ethanol (50 ml), was hydrogenated at ambient temperature and pressure, using 10% palladium on charcoal (0.5 g) as catalyst, until hydrogen uptake ceased. The catalyst was filtered off, washed well with ethanol and the combined filtrate and washings were evaporated to give a colourless oil. This solidified on standing to afford the title compound (5.0 g) as a crystalline solid m.p. 52°–55°.

INTERMEDIATE 14 trans-($\pm$)-2,3-Dihydro-1,4-benzodioxin-2,3-dicarboxylic acid, diethyl ester

Anhydrous Na$_2$CO$_3$ (21.50 g) was added to a solution of Intermediate 13 (18.80 g) in ethanol (500 ml) and the mixture was stirred at ambient temperature for 24 h. The mixture was cautiously acidified with concentrated HCl and evaporated. The residue was then shaken with EA and water, the organic phase was separated and the aqueous layer was further extracted with EA. The combined extracts were dried and evaporated to give a brown oil (19.6 g) containing a 40:60 mixture of cis and trans-diesters. The oil was chromatographed using medium pressure chromatography with a mixture of petroleum ether (b.p. 60°–80°): EA (8:1) as eluant. Fractions containing the less polar trans isomer were combined and evaporated to yield the title compound (9.3 g) as a pale yellow crystalline solid m.p. 54°–56°.

INTERMEDIATE 15 trans-($\pm$)-2,3-Dihydro-1,4-benzodioxin-2,3-dimethanol

A solution of Intermediate 14 (8.56 g) in dry THF (150 ml) was added, over 0.3 h, to an ice-cooled suspension of LiAlH$_4$ (4.40 g) in dry THF (100 ml). The mixture was stirred for a further 0.5 h at 0° then saturated ammonium chloride solution was added dropwise. The mixture was filtered, and the solid was washed well with THF. The combined filtrate and washings were evaporated and the residue partitioned between EA and water. The organic layer was separated and the aqueous layer further extracted with EA. The combined extracts were dried, evaporated and the residue triturated under ER. The solid was collected, washed with ER and dried in vacuo to give the title compound (4.5 g) as a white solid m.p. 119°–120°.

INTERMEDIATE 16 trans-($\pm$)-2,3-Dihydro-1,4-benzodioxin-2,3-dimethanol dimethanesulphonate

A solution of methanesulphonyl chloride (3.60 ml) in CH$_2$Cl$_2$ (100 ml) was added, over 0.25 h, to an ice cooled solution of Intermediate 15 (4.00 g) and triethylamine (8.70 ml) in CH$_2$Cl$_2$ (100 ml). The resulting solution was stirred for a further 0.25 h then washed successively with water, 2N-hydrochloric acid, saturated NaHCO$_3$ and brine. The solution was passed through phase-separating paper and the solvent evaporated. The residue was then triturated under ER, the solid was collected, washed with ER and dried in vacuo to give the title compound (6.7 g) as a white solid m.p. 83°–84°.

EXAMPLE 1

(3aR-trans)-(+)-2-Phenylmethyl-2,3,3a,9a-tetrahydro-1H-[1,4]-benzodioxino[2,3-c]pyrrole, hydrochloride A mixture of Intermediate 4 (3.20 g) and benzylamine (25 ml) was heated at 120° for 0.5 h and the cooled solution poured into EA. The mixture was basified with 2N NaOH and the organic layer was separated. The aqueous layer was further extracted with EA and the combined extracts were dried. Evaporation gave an oil which was dissolved in EA (30 ml) and ER (30 ml) and the solution was acidified with 2N-hydrochloric acid. The precipitate was collected, washed with ER and dried in vacuo to afford the title compound 2.3 g as a white powder m.p. 236°–238° (dec) $[\alpha]_D^{23} = +102.5°$ (c 0.45, H$_2$O). NMR (TFA) $\tau$ 2.42 (s, 5H, CH$_2$Ph), 2.97 (s, 4H, aromatic), 5.32 (d, J6, 2H, CH$_2$Ph), 5.2–6.2 (multiplets, 6H, C1—H$_2$, C3—H$_2$, C3a—H and C9a—H).

EXAMPLE 2

(3aR-trans)-(+)-2,3,3a,9a-Tetrahydro-1H-[1,4]-benzodioxino[2,3-c]pyrrole, hydrochloride A suspension of the compound of Example 1 (2.00 g) in methanol (100 ml) was hydrogenolised at ambient temperature and pressure, using 10% palladium on charcoal (0.2 g) as catalyst, until hydrogen uptake ceased. The catalyst was filtered off, washed with methanol and the combined filtrate and washings were evaporated. Crystallisation of the residue from methanol gave the title compound 0.71 g as off white prisms m.p 271°–274°. $[\alpha]_D^{23} = +154.3°$ (c 0.73, dmso). NMR (dmso-d$_6$) $\tau$ 2.99 (s, 4H, aromatic), 5.59 (m, 2H, C3a—H and C9a—H), 6.19 and 6.71 (2m, 4H, C$_1$—H$_2$ and C$_3$—H$_2$).

EXAMPLE 3

(3aS-trans)-(−)-2-Phenylmethyl-2,3,3a,9a-tetrahydro-1H-[1,4]-benzodioxino[2,3-c]pyrrole, hydrochloride A mixture of Intermediate 10 (3.0 g) and benzylamine (15 ml) was heated at 120° for 0.5 h and the cooled solution poured into EA. The mixture was basified with 2N NaOH and the organic layer was separated. The aqueous layer was further extracted with EA and the combined extracts were passed through a phase separation paper. Evaporation gave an oil which was dissolved in EA (20 ml) and ER (20 ml) and the solution was acidified with 2N-hydrochloric acid. The precipitate was collected, washed with ER and dried in vacuo to afford the title compound 2.52 g as white plates. m.p. 238°–240°, $[\alpha]_D^{21} = -98.18°$ (c 0.34, H$_2$O) NMR (TFA) $\tau$ 2.38 (s, 5H, CH$_2$Ph) 2.95 (s, 4H, aromatic), 5.3 (d, J6, 2H, CH$_2$Ph), 5.2-6.2 (multiplets, 6H, C$_1$—H$_2$, C$_3$—H$_2$, C3a—H and C9a—H).

EXAMPLE 4

(3aS-trans)-(−)-2,3,3a,9a-Tetrahydro-1H-[1,4]-benzodioxino[2,3-c]pyrrole, hydrochloride A solution of the compound of Example 3 (2.4 g) in methanol (120 ml) was hydrogenated at ambient temperature and pressure, using 10% palladium on charcoal (0.24 g) as catalyst, until hydrogen uptake ceased. The catalyst was filtered off, washed well with methanol and the combined filtrate and washings were evaporated. Crystallisation of the residue from methanol afforded the title compound 1.0 g as white prisms m.p. 272°-276°, [α]$_D$= −151.4° (c, 0.74, DMSO), NMR (dmso-d$_6$) τ 2.9 to 3.1 (m, 4H, aromatic), 5.63 (m, 2H, C$_{3a}$—H and C$_{9a}$—H), and 6.22 and 6.72 (two multiplets, each 2H, C$_1$—H$_2$ and C$_3$—H$_2$).

EXAMPLE 5

(a) (±)
trans-2-Methyl-2,3,3a,9a-tetrahydro-1H-[1,4]-benzodioxino[2,3-c]pyrrole, hydrochloride Intermediate 16 (2.00 g) and methylamine (10 ml) were placed in a sealed glass tube and the mixture was heated at 110° for 3 h. After opening, the tube was left at room temperature overnight to remove excess methylamine. The residue was dissolved in methanol and the solution evaporated. The solid obtained was partitioned between a mixture of 2N—NaOH (10 ml), water (5 ml) and EA (20 ml) and the organic phase was separated. The aqueous layer was further extracted with EA and the combined extracts were dried and evaporated to give a pale brown crystalline solid. This was dissolved in a mixture of ER (10 ml) and EA (3 ml) and the solution filtered. The filtrate was then acidified with ethereal hydrogen chloride and the precipitate was collected, washed well with ER and dried in vacuo. Crystallisation from EA-methanol yielded the title compound (0.44 g) as needles. NMR (dmso-d6) τ 2.9-3.1 (m, 4H, aromatic), 5.3-5.6 (m, 2H, C3a—H and C9a—H), 6.05 and 6.42 (m, 4H, C1—H$_2$ and C3—H$_2$), 6.98 (s, 3H, N—Me).

The following compounds were prepared using a similar procedure:

(b) (±)
trans-2-Ethyl-2,3,3a,9a-tetrahydro-1H-[1,4]-benzodioxino[2,3-c]pyrrole, hydrochloride From Intermediate 16 and ethylamine. The product was obtained as pink prisms 0.84 g m.p. 240°-245° (isopropyl alcohol), NMR (dmso-d$_6$) τ 2.97 (s, 4H, aromatic), 5.0 to 5.8 and 5.8-6.8 (multiplets, 7H,N+H, C$_1$—2H, C$_3$—2H, C$_{3a}$—H and C$_{9a}$—H), 6.63 (q, 7 Hz, 2H, NCH$_2$CH$_3$), 8.68 (t, 7 Hz, 3H, NCH$_2$CH$_3$).

(c) (±)
trans-2-Cyclopropyl-2,3,3a,9a-tetrahydro-1H-[1,4]benzodioxino[2,3-c]pyrrole, hydrochloride From Intermediate 16 and cyclopropylamine. The crude free base was dissolved in a mixture of EA (20 ml) and ER (20 ml) and the solution was acidified with 2N-hydrochloric acid. The precipitate was collected, washed with ER, then EA and dried in vacuo to yield the title compound 0.99 g as white microcrystals m.p. 204°-205°. NMR (TFA) τ 2.98 (s, 4H, aromatic), 5.0-6.6 (multiplets, 6H, C$_1$—2H, C$_3$—2H, C$_{3a}$—H and C$_{9a}$—H), 6.80 (m, 1H, cyclopropyl CH), 8.4-9.1 (m, 4—H, cyclopropyl CH$_2$).

(d) (±)
trans-2-(Cyclopropylmethyl)-2,3,3a,9a-tetrahydro-1H-[1,4]-benzodioxino[2,3-c]pyrrole, hydrochloride.

From Intermediate 16 and aminomethylcyclopropane. The crude free base was dissolved in EA (40 ml) and the solution acidified with 2N-hydrochloric acid. The precipitate was collected, washed with EA and dried in vacuo to afford the title compound 1.16 g, as white microcrystals m.p. 243°-246°. NMR (TFA) τ 2.97 (s, 4H, aromatic), 5.1-6.7 (multiplets, 8H, C$_1$—2H, C$_3$—2H, C$_{3a}$—H, C$_{9a}$—H and

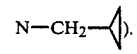

8.70 (m, 1H, cyclopropyl CH), 8.9-9.6 (m, 4H, cyclopropyl CH$_2$).

(e) (±)
trans-2,3,3a,9a-Tetrahydro-2-(2-propenyl)-1H-[1,4]-benzodioxino[2,3-c]pyrrole, hydrochloride From Intermediate 16 and allylamine. After trituration with isopropyl alcohol the product was obtained as a buff powder 1.2 g. m.p. 234°-236°. NMR (dmso-d$_6$) τ 2.97 (s, 4H, aromatic), 3.7-4.2 (m, 1H, NCH$_2$CH=CH$_2$), 4.2-4.6 (m, 2H, NCH$_2$CH=CH$_2$), 5.5 (m, broad), 2H, C$_{3a}$—H and C$_{9a}$—H), 5.8-7.2 (multiplets, 6H, C$_1$—2H, C$_3$—2H and N—CH$_2$CH=CH$_2$).

EXAMPLE 6

(±)
trans-2,3,3a,9a-Tetrahydro-2-phenylmethyl-1H-[1,4]-benzodioxino[2,3-c]pyrrole, hydrochloride A mixture of Intermediate 16 (2.00 g) and benzylamine (10 ml) was heated at 120° for 0.5 h and the cooled solution poured into EA. The mixture was basified with 2N NaOH and the organic layer was separated. The aqueous layer was further extracted with EA and the combined extracts were dried. Evaporation gave an oil which was dissolved in EA (20 ml) and ER (20 ml) and the solution was acidified with 2N-hydrochloric acid. The precipitate was collected, washed with ER and dried in vacuo to afford the title compound (1.3 g) as white plates. NMR (TFA) τ 2.47 (s, 5H, CH$_2$Ph), 3.03 (s, 4H, aromatic), 5.38 (d, 2H, CH$_2$Ph), 5.2-6.2 and 6.48 (multiplets, 6H, C$_1$—H$_2$, C$_3$—H$_2$, C3a—H and c9a—H).

EXAMPLE 7

(±)
trans-2,3,3a,9a-Tetrahydro-1H-[1,4]-benzodioxino[2,3-c]pyrrole, hydrochloride A solution of the compound of Example 6 (1.00 g) in methanol (50 ml) was hydrogenated at ambient temperature and pressure, using 10% palladium on charcoal (0.10 g) as catalyst, until hydrogen uptake ceased. The catalyst was filtered off, washed well with methanol and the combined filtrate and washings were evaporated. Crystallisation of the residue from methanol afforded the title compound (0.43 g) as white prisms m.p. 271°-274°. NMR (dmso-d6) τ 2.99 (s, 4H, aromatic), 5.59 (m, 2H, C3a—H and C9a—H), 5.9-6.4 and 6.5-6.9 (2m, 4H, C1—H$_2$ and C3—H$_2$).

EXAMPLE 8

(±)
trans-2,3,3a,9a-Tetrahydro-2-propyl-1H-[1,4]-benzodioxino[2,3-c]pyrrole, hydrochloride A solution of the compound of Example 5(e) (0.60 g) in methanol (50 ml) was hydrogenated at ambient temperature and pressure, using 10% palladium on charcoal (0.06 g) as catalyst until hydrogen uptake ceased. The catalyst was filtered off, washed well with methanol and the combined filtrate and washings were evaporated. The residue was triturated under isopropyl alcohol, the solid was collected, washed with isopropyl alcohol and dried in vacuo to yield the title compound 0.35 g as an off-white crystalline solid m.p. 243°–245° NMR (dmso-$d_6$) $\tau$ 3.02 (s, 4H, aromatic), 5.56 (m, 2H, $C_{3a}$ and $C_{9a}$—H), 5.9–6.9 (multiplets, 6H, $C_1$—2H, $C_3$—2H and N—CH$_2$CH$_2$CH$_3$), 8.26 (m, 2H, NCH$_2$CH$_2$CH$_3$), and 9.06 (t, 3H, NCH$_2$CH$_2$CH$_3$).

EXAMPLE 9

(±)
trans-2,3,3a,9a-Tetrahydro-2-(2-propynyl)-1H-[1,4]-benzodioxino[2,3-c]pyrrole, hydrochloride A solution of propargylbromide (0.7 ml of an 80% w/w solution in toluene) in ethanol (5 ml) was added to a mixture of the compound of Example 7, free base (1.1 g) and potassium carbonate (1.1 g) in ethanol (15 ml), over 0.3 h. The mixture was stirred at ambient temperature for 3 h, then heated at 90° for 1 h and the cooled mixture was evaporated. The residue was partitioned between EA and water, and the aqueous phase separated. This was further extracted with EA and the combined extracts evaporated. The residue was dissolved in EA and the solution was washed with 2N-hydrochloric acid. The acid washings were made basic with 10N—NaOH and the resulting mixture was extracted with EA. Evaporation of the organic extracts gave a residue which was dissolved in a mixture of EA (25 ml) and ER (10 ml) and the solution was acidified with ethereal hydrogen chloride. The precipitate was collected, washed first with ER, then isopropyl alcohol and then dried in vacuo. Crystallisation from ethanol gave the title compound 0.44 g as pale brown plates m.p. 211°–213°. NMR (dmso-$d_6$) $\tau$ 2.98 (s, —4H, aromatic), 5.3–5.8 (m, 4H, $C_{3a}$—H, $C_{9a}$—H and NCH$_2$C≡CH), 5.8 to 6.6 (multiplets, 4H, $C_1$ and $C_3$—CH$_2$), and 6.20 (t, 2 Hz, 1H, C≡CH).

EXAMPLE 10

(±)
trans-2,3,3a,9a-Tetrahydro-1H-[1,4]-benzodioxino[2,3-c]pyrrole-2-carboxaldehyde A solution of the compound of Example 7, free base (2.0 g) in methyl formate (15 ml) was stirred at ambient temperature for 2 h and the resulting mixture was evaporated. The residue was triturated under ER, and the solid was collected, washed with ER and dried in vacuo to afford the title compound 2.2 g as white microcrystals m.p. 207°–208°. NMR (TFA) $\tau$ 1.53 (s, 1H, NCHO), 3.00 (s, 4H, aromatic), 5.3–5.8 and 5.9–6.6 (multiplets, 6H, $C_1$—2H, $C_3$—2H, $C_{3a}$—H and $C_{9a}$—H).

EXAMPLE 11

(±)
trans-2,3,3a,9a-Tetrahydro-2-methyl-1H-[1,4]-benzodioxino[2,3-c]pyrrole, hydrochloride The compound of Example 10 (1.50 g) was added, in portions, to an ice cooled suspension of LiAlH$_4$ (0.64 g) in THF (50 ml) and the resulting mixture was stirred at ambient temperature for 3.5 h then heated under reflux for 2 h. The mixture was cooled in ice and excess LiAlH$_4$ was destroyed by the addition of water. The mixture was filtered and the solid washed with THF. The combined filtrate and washings were evaporated and the residue partitioned between EA and 2N—NaOH. The aqueous phase was separated and further extracted with EA. The combined extracts were dried and evaporated to give a white, crystalline solid (1.28 g). A portion (0.88 g) of the solid was dissolved in ER (10 ml) and the solution was acidified with ethereal hydrogen chloride. The solid was collected and crystallised twice (methanol/ethyl acetate) to give the title compound 0.51 g as a white crystalline solid. NMR (dmso-d6) $\tau$ 2.9–3.1 (m, 4H, aromatic), 5.3–5.6 (m, 2H, $C_{3a}$—H and $C_{9a}$—H), 6.05 and 6.42 (m, 4H, $C_1$—H$_2$ and $C_3$—H$_2$), 6.98 (s, 3H, N—Me).

PHARMACEUTICAL EXAMPLES

Pharmaceutical compositions according to the invention may be formulated in accordance with the following instructions.

In these Examples, "Active Ingredient" refers to (±) trans 2,3,3a,9a-tetrahydro-1H-[1,4]-benzodioxino-[2,3-c]pyrrole hydrochloride. Other compounds of the invention may be formulated in similar fashion.

| 1. Oral Capsule | per capsule |
| --- | --- |
| Active Ingredient | 50 mg |
| Magnesium stearate | 0.5 mg |
| Anhydrous lactose | 50 mg |

Blend the active ingredient with the lactose and magnesium stearate. Fill the blend into appropriate size hard gelatin capsules (lock fitting type) on an automatic capsule filling machine.

| 2. Oral Syrup | per 5 ml dose |
| --- | --- |
| Active Ingredient | 50 mg |
| Sodium citrate | 25 mg |
| Citric acid | to pH 4.5 |
| Sunset yellow FCF (Dye) | 0.25 mg |
| Methyl hydroxybenzoate sodium | 5.0 mg |
| Propyl hydroxybenzoate sodium | 2.0 mg |
| Liquid orange flavour | qS |
| Sucrose | 3.25 g |
| Purified water | to 5.0 ml |

Dissolve the sucrose in a minimum quantity of water. Add a concentrated solution of sodium citrate with stirring and adjust the pH to 4.5 with citric acid. With continued stirring, add a 10% aqueous solution of the active ingredient, followed by a solution of the dye, a solution of the hydroxybenzoates and lastly the flavour. Adjust almost to volume with water and stir. Check the pH and adjust to 4.5 with citric acid if necessary. Make up to volume with water.

| 3. | Oral Tablet | per tablet |
|---|---|---|
| | Active ingredient | 50 mg |
| | Polyvinylpyrrolidone | 4.0 mg |
| | Sodium starch glycollate | 10.0 mg |
| | Magnesium stearate | 2.0 mg |
| | Lactose to tablet core weight of | 200 mg |

Blend the active ingredient with the lactose. Add a sufficient quantity of polyvinylpyrrolidone solution to produce a damp mass suitable for granulation. Prepare the granules and dry using a tray of fluid bed dryer. Pass through a sieve, blend with the remaining ingredients and compress into 8 mm diameter tablets on a tablet machine.

Film coat the tablet cores with hydroxypropyl methyl cellulose or similar film forming material, using either an aqueous or non-aqueous solvent system. A plasticizer and suitable colour may be included in the film coating solution.

We claim:

1. A compound selected from the group consisting of compounds of formula (I):

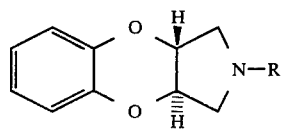
(I)

wherein R is a hydrogen atom or a $C_{1-6}$ alkyl (optionally substituted by $C_{3-7}$ cycloalkyl), $C_{3-6}$ alkenyl, $C_{3-6}$ alkynyl, $C_{3-7}$ cycloalkyl, aralkyl (in which the alkyl moiety contains 1–5 carbon atoms), or —CHO group, and physiologically acceptable salts thereof.

2. A compound according to claim 1, wherein R is a hydrogen atom.

3. A compound according to claim 1, wherein R is selected from the group consisting of a methyl group, an ethyl group and a cyclopropyl group.

4. (±) trans-2,3,3a,9a-Tetrahydro-2-methyl-1H-[1,4]-benzodioxino[2,3-c]pyrrole and its physiologically acceptable salts.

5. A compound selected from the group consisting of (±) trans-2,3,3a,9a-tetrahydro-1H-[1,4]-benzodioxino-[2,3-c]pyrrole and its physiologically acceptable salts.

6. A compound selected from the group consisting of (3aR-trans)-(+)-2,3,3a,9a-tetrahydro-1H-[1,4]-benzodioxino[2,3-c]pyrrole; (3aS-trans)-(+)-2,3,3a,9a-tetrahydro-1H-[1,4]-benzodioxino[2,3-c]pyrrole; and their physiologically acceptable salts.

7. A compound according to claim 1, wherein the physiologically acceptable salt is selected from the group consisting of a hydrochloride, hydrobromide, phosphate, sulphate, citrate, tartrate, acetate, maleate and succinate.

8. (±) trans-2,3,3a,9a-Tetrahydro-1H-[1,4]-benzodioxino[2,3-c]pyrrole, hydrochloride.

9. A $\alpha_2$-adrenoreceptor antagonist composition comprising a compound selected from the group consisting of compounds of formula (I), physiologically acceptable salts thereof and their mixtures together with a physiologically acceptable carrier or excipient.

10. A $\alpha_2$-adrenoreceptor composition according to claim 9, which also comprises an established antidepressant.

11. A process for the preparation of a compound of formula (I) as defined in claim 1 or a physiologically acceptable salt thereof which comprises A. aminating a compound of formula (II):

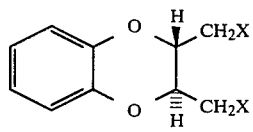
(II)

where X is a leaving group with ammonia, aqueous ammonia or an amine of formula $RNH_2$, (where R is as defined in claim 1 except that R is not a hydrogen atom or the group —CHO); or B. in order to prepare a compound of formula (I) where R represents a hydrogen atom, deprotecting a corresponding compound where R represents a protecting group; or C. in order to prepare a compound of formula (I) where R represents an alkyl group, reducing the corresponding compound where R represents an acyl group;

and, if desired, subjecting the compound thus obtained to one or two further reactions comprising D. (i) converting the resulting compound of formula (I) or a salt thereof into another compound of formula (I) and/or (ii) converting a compound of formula (I) or a salt thereof into a physiologically acceptable salt thereof.

* * * * *